United States Patent [19]

Anders et al.

[11] 4,328,181

[45] May 4, 1982

[54] INDICATOR MATERIAL

[75] Inventors: Leon W. Anders, Woodbury; David C. Weigel, White Bear Lake, both of Minn.

[73] Assignee: Minnesota Mining and Manufacturing Co., St. Paul, Minn.

[21] Appl. No.: 55,146

[22] Filed: Jul. 6, 1979

[51] Int. Cl.$^3$ .................... G01N 21/78; G01N 31/22
[52] U.S. Cl. .................... 422/56; 23/230 R; 23/232 R; 73/23; 116/206; 252/408; 422/57; 422/58; 422/60; 422/86
[58] Field of Search ......... 252/408; 23/230 R, 232 R; 73/23; 422/56, 57, 58, 55, 60, 86; 116/206

[56] References Cited

U.S. PATENT DOCUMENTS

| | | | |
|---|---|---|---|
| 2,174,349 | 9/1939 | Littlefield | 23/232 R |
| 2,738,257 | 3/1956 | Darby | 252/408 |
| 2,864,725 | 12/1958 | Sorg et al. | 422/57 |
| 3,112,999 | 12/1963 | Grosskopf | 422/57 |
| 3,451,741 | 6/1969 | Manos | 252/408 |
| 3,528,780 | 9/1970 | Radawski | 252/408 |
| 3,545,930 | 12/1970 | Walker et al. | 252/408 |
| 3,574,552 | 4/1971 | Rakowski | 23/232 R |
| 4,115,067 | 9/1978 | Lyshkow | 252/408 |
| 4,169,811 | 10/1979 | Yoshikawa et al. | 23/232 R |
| 4,222,745 | 9/1980 | Cloyd | 252/408 |
| 4,256,694 | 3/1981 | McAllister et al. | 252/408 |

FOREIGN PATENT DOCUMENTS 496345 11/1938 United Kingdom .................. 422/57

*Primary Examiner*—Teddy S. Gron
*Attorney, Agent, or Firm*—Cruzan Alexander; Donald M. Sell; Edward T. Okubo

[57] ABSTRACT

Indicator material for monitoring personal exposure to hazardous substances in ambient air comprising a pigment material, a binder and a sensitizer coated upon a transparent support member as a porous coating which permits gaseous diffusion throughout the coating is disclosed. Detection or monitoring is effected when the indicator material undergoes a visually observable reaction with hazardous material in the atmosphere at room temperature.

16 Claims, No Drawings

INDICATOR MATERIAL

BACKGROUND OF THE INVENTION

The present invention relates to indicator material particularly suited for monitoring personal exposure to hazardous materials such as hydrogen sulfide ($H_2S$), sulfur dioxide ($SO_2$) and chlorine ($Cl_2$). The indicator material is a composition comprising a pigment material, a sensitizer material and a binder component coated upon a transparent support member. Detection or monitoring is effected when the composition undergoes a visually observable reaction with the hazardous material in the atmosphere at room temperature.

Devices for monitoring exposure to hazardous material based on color change of a sensitizer are currently available. The exposure level is usually determined by comparing the color density of the exposed sensitizer with a standard final color density value. If the sensitizer is in or on an opaque or translucent medium, the color comparison is made on the side exposed to the hazardous material. If the sensitizer is on or in a transparent medium, it is then possible to make the comparison from either side. In either case, the change in color density is initially very rapid and then becomes gradual as it reaches its final density value. This final, gradual change makes it difficult to determine the exact exposure endpoint, i.e., when the sensitizer has reached its final color density value.

Prior workers have directed their attention to monitoring personal exposure to hazardous materials. See for example, Natusch, Sewell and Tanner, "Determination of $H_2S$ in Air–An Assessment of Impregnated Paper Tape Methods," *Analytical Chemistry*, volume 46, page 3 (1974); Schnakenberg, "A passive Personal Sampler for Nitrogen Dioxide," *Bureau of Mines Technical Progress Report* 95 (1976); Ray, Carroll and Armstrong, "Evaluation of Small Color-Changing Carbon Monoxide Dosimeters," *Bureau of Mines Rep. Invest.* (1975); Palmer, "Personal Samplers for CO, NO and $NO_2$ in Air," *Bureau of Mines Report OFR* 92-77 (1977) and Nichols, "Reactive Tapes for Automatic Environmental Analysis, Personal Vapor Monitoring Badges for Industrial Workers," *National Science Foundation Report NSF/RA*-780039 (1978).

SUMMARY OF THE INVENTION

The indicator material of the present invention is a composition comprising a pigment material, a sensitizer and a binder coated onto a transparent support member as a porous coating permitting gaseous diffusion throughout the coating, in which form the indicator material provides qunatitative monitoring of gaseous contaminants in ambient atmosphere at room temperature. The pigment gives the coating opacity or hiding power and also serves as a substrate for the sensitizer. The binder serves to hold the pigment particles together and also bonds the indicator marterial to the support member.

The indicator coating must allow diffusion of the hazardous material into the coating for its subsequent reaction with the sensitizer and formation of an image (an area with a change in some measurable property). Within the coating, the reaction between the hazardous material and sensitizer preferably occurs rapidly and irreversibly. The product of this reaction forms a progressively thicker layer in the coating which is distinct from the unreacted sensitizer remaining in the coating. Therefore, with longer or greater contaminant exposure, the thickness of the reaction layer will increase and progress through the depth of the coating until it finally reaches the film backing side. When the image formed by the reaction process progresses to the film backing side, the exposure endpoint has been reached. This exposure endpoint, viewed from the film backing side, can be readily visually resolved by an observer since the image development occurs very rapidly as it approaches its final value, i.e., the initial change (color) in the coating is gradual and becomes more rapid as development approaches its endpoint.

DETAILED DESCRIPTION OF THE INVENTION

The desirability of devices for personal monitoring of exposure to specific hazardous materials in the environment has been unquestionably established and, in fact, is required for many specific materials by governmental regulations. It is also desirable and, in some instances, required that such devices indicate when exposure to a specific hazardous material has reached a selected time-weighted-average value.

The indicator material of the present invention is a composition containing a sensitizer which will react with a specific hazardous material. The product of this reaction forms an image such that the "permitted" exposure to the specific contaminant can be easily quantitatively resolved as a distinct endpoint.

The indicator material of the present invention, in the form of a coating, comprises not only a sensitizer but also a pigment and a binder. The pigment gives the coating opacity or hiding power and also serves as a substrate for the sensitizer. Among the useful pigments are the white pigments such as alumina, silica, titanium dioxide, barium titanate, zinc oxide, etc. or those colored pigments such as lead chromate, chromium oxide, etc. These pigments may be used singly or in combination in order to achieve the desired imaging properties.

The selectivity and sensitivity of the indicator coating for a particular contaminant is dependent on the selection of an appropriate sensitizer. For example, hydrogen sulfide can be detected by the addition of a metallic ion which will form a metallic sulfide image. Sulfur dioxide will react and form an image with indophenol and chlorine will react with N-benzoyl leuco methylene blue.

The binder can be an organic or an inorganic material which is capable of holding the particles together and also bond the coating to the film backing.

The unique feature of the indicator coating construction of the present invention is its ability to readily quantitatively resolve the exposure endpoint when viewed from the film backing side. The difference in the development rate of an image to its final value as viewed from both sides of the coating is depicted in Table 1, where the reflectance color density of the image is shown as a function of exposure. The reflectance color density was measured with a Macbeth Reflectance Densitometer, Model RD 514. The indicator coating comprised 81.7% alumina as the pigment, 2% gelatin as the binder, 4.1% silver nitrate as the sensitizer and 12.2% concentrated nitric acid as stabilizer for the silver nitrate. The alumina pigment was Alcoa F-1, a high surface area alumina, which was ball milled to fine particles. The coating indicator composition was coated (2.20 g/ft$^2$) onto a polyester film support member and placed as the collector in a monitor such as described in Braun U.S. Pat. No. 4,158,958; the test device had a cylindrical diffusional chamber with a one centimeter diameter and a height of one centimeter. This test device was exposed to air which contained 35 ppm hydrogen sulfide.

TABLE 1

| Percent of Exposure | Measured from Exposed Side | | Measured from Film Side | |
|---|---|---|---|---|
| | Exposure Time (min) | Reflectance Density | Exposure Time (min.) | Reflectance Density |
| 0 | 0 | .07 (0%) | 0 | .18 (0%) |
| 10 | 2 | .20 (33%) | 2.5 | .18 (0%) |
| 20 | 4 | .29 (56%) | 5.0 | .19 (3%) |
| 30 | 6 | .35 (72%) | 7.5 | .10 (6%) |
| 40 | 8 | .39 (82%) | 10.0 | .22 (13%) |
| 50 | 10 | .42 (90%) | 12.5 | .23 (16%) |
| 60 | 12 | .43 (92%) | 15.0 | .26 (25%) |
| 70 | 14 | .44 (95%) | 17.5 | .30 (38%) |
| 80 | 16 | .45 (97%) | 20.0 | .36 (56%) |
| 90 | 18 | .45 (97%) | 22.5 | .44 (81%) |
| 100 | 20 | .46 (100%) | 25.0 | .50 (100%) |

In Table 1, the reflectance color density, as measured from the side of the coating exposed to hydrogen sulfide and as measured from the film backing side is tabulated as a function of the exposure time. From a comparison of these data, it is evident that the final density value in each case is developed quite differently.

When the indicator material is used in a monitoring device for measuring exposure to specific hazardous materials, exposure endpont is measured by the final color density. In such devices, it is desirable if the exposure endpoint can be independently visually resolved without resort to extraneous indicia such as a color standard. The ability of an observer to independently determine the endpoint depends, of course, on his ability to visually resolve the final color density.

If the observer can resolve the final change in reflectance density to a value of 0.01 units, he should be able to resolve the endpoint within 4 minutes when viewing the image from the exposed side and within 0.5 minute when viewing from the film backing side as shown by the data in Table 2. This amount of exposure is 20% of the total exposure in the first case and only 2% in the latter. Also tabulated are additional values assuming that the observer can only resolve the final density value over a larger range. It will be noted that on the exposed side, the final 12.5% change in color density required 55% of the total exposure, but only required 5.6% of the total exposure when viewed from the film backing side. From this comparison, it is evident that the indicator coating construction of the present invention allows the exposure endpoint or final color density to be resolved over a very narrow exposure range.

TABLE 2

| Measured From Exposed Side | | | |
|---|---|---|---|
| Range of Final Change in Reflectance Density | Percent of Total Change | Length of Exposure (min) | Percent of Total Exposure |
| .45–.46 (.01) | 2.5 | 4 | 20 |
| .44–.46 (.02) | 5.0 | 6 | 30 |
| .43–.46 (.03) | 7.5 | 8 | 40 |
| .42–.46 (.04) | 10.0 | 10 | 50 |
| .41–.46 (.05) | 12.5 | 11 | 55 |
| Measured From Film Side | | | |
| Range of Final Change in | Percent of | Length of Exposure | Percent of |

TABLE 2-continued

| Reflectance Density | Total Change | (min) | Total Exposure |
|---|---|---|---|
| .49–.50 (.01) | 3.0 | .5 | 2.0 |
| .48–.50 (.02) | 6.3 | .8 | 3.2 |
| .47–.50 (.03) | 9.4 | 1.1 | 4.4 |
| .46–.50 (.04) | 12.5 | 1.4 | 5.6 |
| .45–.50 (.05) | 15.6 | 1.7 | 6.8 |

A granular activated alumina, F-1 from Alcoa (Aluminum Company of America) was ball milled in a water slurry containing 33% solids to a particle size range as tabulated in Table 3.

TABLE 3

| Particle Size Distribution | Particle Diameter (Microns) |
|---|---|
| 95% > | .6 |
| 84% > | .7 |
| 75% > | .9 |
| 50% > | 1.3 |
| 25% > | 2.5 |
| 16% > | 3.5 |
| 5% > | 6.7 |

The particle size distribution was measured by adding a few drops of the ball milled solution to 10 ml of a 1% sodium pyrophosphate water solution. The diluted sample was agitated in an ultrasonic bath for 1 to 5 minutes. This was further diluted into electrolyte and sonified for 1 to 2 minutes prior to counting.

Counting was done on a Coulter Counter Model TA II, using standard techniques. Apertures of 200 millimicron, 70 millimicron and 30 millimicron were used to cover the entire breadth of the distribution as required. The electrolyte used was 2% sodium chloride plus 30% glycerine in water for the 200 millimicron aperture, and 5% sodium chloride in water for the 70 millimicron and 30 millimicron apertures. The lower detection limit in all cases is 0.5 millimicron.

600 g of the above slurry was acidified with 30 g of concentrated nitric acid to stabilize the sensitizer. This slurry was sensitized with 10 cc of a silver nitrate solution which contained 1 gram of silver nitrate per cubic centimeter of solution. The above sensitized slurry was then diluted with 200 g of ethanol. A binder solution was prepared by dissolving 100 g of gelatin, (Photographic Gelatin 1312 from Kind & Knox Gelatin) into 400 g of a warm water solution containing 25% ethanol. Coating dispersions with varying ratios of alumina pigment to gelatin binder were prepared by warming each solution to 55°–60° C. and combining an appropriate amount of the gelatin solution with pigment dispersion while stirring with a propeller driven by an air motor. The formulations for the coating solutions are tabulated in Table 4.

TABLE 4

| Pigment Dispersion | |
|---|---|
| 600 g | Pigment dispersion (33% Alumina, Alcoa F-1 in water) |
| 30 g | Acid (concentrated Nitric Acid) |
| 10 cc | Sensitizer solution (1 g $AgNo_3$/cc) |
| 200 g | Ethanol |
| Binder Solution | |
| 100 g | Gelatin (Photographic 1312, Kind & Knox) |
| 100 g | Ethanol |
| 300 g | Water |

| Coating Dispersions | | | | |
|---|---|---|---|---|
| Disper- | Ratio | Percent Alumina In Dis- | Pigment | Gelatin |

TABLE 4-continued

| sion | Pigment/Binder | Coating | persion | Solution | Water |
|---|---|---|---|---|---|
| A | 2.5/1 | 71.4 | 85 g | 40 g | — |
| B | 5/1 | 83.3 | 85 g | 20.0 g | — |
| C | 10/1 | 90.0 | 85 g | 10.0 g | 5.0 g |
| D | 20/1 | 95.2 | 85 g | 5.0 g | 10.0 g |
| E | 40/1 | 97.5 | 85 g | 2.5 g | 12.5 g |

Samples with various coating weights of a sensitized coating were prepared by coating these dispersions on a corona primed polyester film with a laboratory knife coater. After initial drying with hot air, samples were placed in an oven and dried for eight hours at 65° C. Samples with similar coating weights were selected and exposed to air containing 35 ppm hydrogen sulfide using the monitoring device described above. With a Macbeth Reflectance Densitometer, the reflectance density was measured as a function of the exposure time. The results are reported in Table 5.

TABLE 5

| | COATING B | | COATING C | | COATING D | | COATING E | |
|---|---|---|---|---|---|---|---|---|
| Percent of Exposure | Exposure Time (Min.) | Reflectance Density | Exposure Time (Min.) | Reflectance Density | Exposure Time (Min.) | Reflectance Density | Exposure Time (Min.) | Reflectance Density |
| 0 | 0 | .23 (0%) | 0 | .23 (0%) | 0 | .22 (0%) | 0 | .22 (0%) |
| 10 | 4.5 | .24 (6%) | 7.5 | .23 (0%) | 8.5 | .22 (0%) | 9.2 | .22 (0%) |
| 20 | 9.0 | .26 (17%) | 15.0 | .24 (4%) | 17.0 | .23 (4%) | 18.4 | .22 (0%) |
| 30 | 13.5 | .28 (28%) | 22.5 | .25 (8%) | 25.5 | .23 (4%) | 27.6 | .23 (3%) |
| 40 | 18.0 | .30 (39%) | 30.0 | .26 (12%) | 34.0 | .24 (7%) | 36.8 | .24 (7%) |
| 50 | 22.5 | .33 (56%) | 37.5 | .28 (20%) | 42.5 | .26 (15%) | 46.0 | .26 (14%) |
| 60 | 27.0 | .35 (67%) | 45.0 | .30 (28%) | 51.0 | .29 (26%) | 55.2 | .29 (24%) |
| 70 | 31.5 | .37 (78%) | 52.5 | .33 (40%) | 59.5 | .32 (37%) | 64.4 | .33 (38%) |
| 80 | 36.0 | .39 (89%) | 60.0 | .38 (60%) | 68.0 | .36 (52%) | 73.6 | .38 (55%) |
| 90 | 40.5 | .40 (94%) | 67.5 | .44 (84%) | 76.5 | .43 (78%) | 82.8 | .44 (76%) |
| 100 | 45.0 | .41 (100%) | 75.0 | .48 (100%) | 85.0 | .49 (100%) | 92.0 | .51 (100%) |

As will be clearly observed from an examination of Table 5, the more desirable image development was obtained when the pigment to binder ratio was 10 to 1 or greater. Sample A with a pigment to binder ratio of 2.5 to 1 would not develop an image.

The surface area (intra-particle porosity) was varied by heating granular activated alumina, RA-1 from Reynolds Chemicals, a division of Reynolds Metals Company, to a high temperature (~950° C.) for varying lengths of time to reduce the surface area. Granules with surface areas of 205 m²/g, 95 m²/g and 40 m²/g were ball milled under similar conditions for the same length of time and used to prepare pigment dispersions as described in Table 4. With these pigment dispersions and the binder solution, coating dispersions were formulated according to E in Table 4. Coated samples were prepared as previously described. Samples with similar coating weights were selected and exposed to air containing 35 ppm hydrogen sulfide with a device as described above. For these samples, the image reflectance density as a function of exposure time is shown in Table 6. Although the pigment surface area (intraparticle porosity) varies in these coatings, the inter-particle porosity should be very similar as all coatings were prepared from the same formulation with the same pigment to binder ratio. From observing the data in Table 6, it is evident that over this variation in pigment surface area (intra-particle porosity), the rate of change in the reflectance density is very similar. Therefore, the ability to form a desirable image appears to be independent of the intra-particle porosity of the pigment.

TABLE 6

| | Pigment Surface Area (205 m²/g) | | Pigment Surface Area (95 m²/g) | | Pigment Surface Area (40 m²/g) | |
|---|---|---|---|---|---|---|
| Percent of Exposure | Exposure Time (Min.) | Reflectance Density | Exposure Time (Min.) | Reflectance Density | Exposure Time (Min.) | Reflectance Density |
| 0 | 0 | .24 (0%) | 0 | .21 (0%) | 0 | .18 (0%) |
| 10 | 8.2 | .25 (3%) | 8.3 | .21 (0%) | 7.8 | .19 (4%) |
| 20 | 16.4 | .26 (5%) | 16.6 | .22 (4%) | 15.6 | .19 (4%) |
| 30 | 24.6 | .27 (8%) | 24.9 | .23 (7%) | 23.4 | .20 (7%) |
| 40 | 32.8 | .28 (11%) | 33.2 | .24 (11%) | 31.2 | .21 (11%) |
| 50 | 41.0 | .31 (19%) | 41.5 | .26 (19%) | 39.0 | .23 (19%) |
| 60 | 49.2 | .33 (24%) | 49.8 | .28 (26%) | 46.8 | .25 (26%) |
| 70 | 57.4 | .38 (38%) | 58.1 | .31 (37%) | 54.6 | .28 (37%) |
| 80 | 65.4 | .42 (49%) | 66.4 | .35 (52%) | 62.4 | .32 (52%) |
| 90 | 73.8 | .51 (73%) | 74.7 | .41 (74%) | 70.2 | .38 (74%) |
| 100 | 82.0 | .61 (100%) | 83.0 | .48 (100%) | 78.0 | .45 (100%) |

Coating dispersions similar to those outlined in Table 4 were prepared with the omission of the acid and sensitizer from the pigment dispersion as the only exception. With these dispersions coatings were made and dried as described above. The surface area of the coating formulations was measured by the Brunauer, Emmett and Teller (BET) method.

TABLE 7

| Coating Formulation | Percent Alumina | Surface Area of Coatings (m²/g) | Theoretical Surface Area of Coatings (m²/g) | Difference in Surface Area (m²/g) | Percent of Surface Area Lost |
|---|---|---|---|---|---|
| A | 71.4 | 45 | 129 | 84 | 65 |
| B | 83.3 | 70 | 150 | 80 | 53 |
| C | 90.0 | 95 | 162 | 67 | 41 |
| D | 95.2 | 120 | 171 | 51 | 30 |
| E | 97.5 | 155 | 176 | 21 | 12 |
| (Alumina | 100.0 | | 180 | 0 | — |

TABLE 7-continued

| Coating Formulation | Percent Alumina | Surface Area of Coatings ($m^2/g$) | Theoretical Surface Area of Coatings ($m^2/g$) | Difference in Surface Area ($m^2/g$) | Percent of Surface Area Lost |
|---|---|---|---|---|---|
| Powder) | | | | | |

The surface area of the coatings results primarily from the intra-particle porosity of the high surface area alumina pigment (180 $m^2/g$) and its availability in the coatings is related to the inter-particle porosity of the coating. The coatings must be sufficiently porous to allow diffusion of the hazardous material into the coating for its subsequent reaction with the sensitizer.

As observed in Table 7, as the percent binder in the coatings increases, coating porosity (surface area) decreases as more of the alumina pigment is covered by the binder, as indicated by an increase in the percent of the surface area which is lost. The percent lost is based on the difference between the measured surface area of the coatings and the theoretical surface area as determined by the product of the percent alumina in the coating and the intra-particle porosity (surface area) of the alumina powder.

Coatings with varying weights were prepared using coating dispersion E described in Table 4. The coatings were prepared and exposed as previously described. In Table 8, the reflectance density is shown as a function of the exposure time.

TABLE 8

| | Coating Weight 1.23 $g/ft^2$ | | Coating Weight 2.06 $g/ft^2$ | | Coating Weight 2.67 $g/ft^2$ | |
|---|---|---|---|---|---|---|
| Percent of Exposure | Exposure Time (Min.) | Reflectance Density | Exposure Time (Min.) | Reflectance Density | Exposure Time (Min.) | Reflectance Density |
| 0 | 0 | .30 (0%) | 0 | .23 (0%) | 0 | .21 (0%) |
| 10 | 3.8 | .31 (5%) | 6.6 | .23 (0%) | 9.0 | .21 (0%) |
| 20 | 7.6 | .32 (10%) | 13.2 | .24 (4%) | 18.0 | .22 (3%) |
| 30 | 11.4 | .33 (15%) | 19.8 | .25 (7%) | 27.0 | .23 (6%) |
| 40 | 15.2 | .34 (20%) | 26.4 | .26 (11%) | 36.0 | .25 (13%) |
| 50 | 19.0 | .36 (27%) | 33.0 | .28 (18%) | 45.0 | .27 (20%) |
| 60 | 22.8 | .38 (36%) | 39.6 | .31 (29%) | 54.0 | .29 (27%) |
| 70 | 26.6 | .41 (50%) | 46.2 | .35 (43%) | 63.0 | .33 (40%) |
| 80 | 30.4 | .46 (73%) | 52.8 | .40 (61%) | 72.0 | .37 (53%) |
| 90 | 34.2 | .50 (91%) | 59.4 | .46 (82%) | 81.0 | .45 (80%) |
| 100 | 38.0 | .52 (100%) | 66.0 | .51 (100%) | 90.0 | .51 (100%) |

From the data in Table 8, it is evident that image development is improved with increased coating weight. This can be verified by observing that the final 10% of the exposure caused the reflectance density to change 9%, 18% and 20% for the coating weights 1.23 $g/ft^2$, 2.06 $g/ft^2$ and 2.67 $g/ft^2$, respectively. Also, the absolute length of exposure necessary for each coating to reach its endpoint or maximum reflectance density is a function of the coating weight. The change in reflectance density from the initial to final value also increases with increasing coating weight.

Coating dispersions were prepared as described for formulation E in Table 4 where the concentration of the silver nitrate was varied in preparing sensitized pigment dispersions. Coatings with 5, 5.3 and 8 percent silver nitrate were prepared. These coatings were exposed to air containing 35 ppm hydrogen sulfide in a monitoring device as described previously. The time to reach the final and maximum reflectance density of the image, measured as a function of sensitizer concentration, is reported in Table 9.

TABLE 9

| Percent Silver Nitrate in Coating | Exposure Time per Unit Coating Weight to Reach Maximum Reflectance Density (min/g/$ft^2$) |
|---|---|
| 8 | 52 |
| 5.3 | 35 |
| 5.0 | 33 |

Examination of Tables 8 and 9 will reveal that the time required for a constant exposure to form an image is not only a function of the coating weight but is also a function of the silver nitrate concentration.

A coating dispersion was prepared by acidifying 50 grams of a 40% lead chromate dispersion with 5 drops of concentrated nitric acid solution and then sensitized with 1 cc of silver nitrate solution (1 g/cc). The above was combined with 3.3 grams of a 20% gelatin solution. This dispersion was coated (4.2 $g/ft^2$), dried and exposed to air containing 35 ppm hydrogen sulfide as previously described. The reflectance density was measured from both sides of the coating. The results are shown in Table 10.

Another coating dispersion was prepared by acidifying 100 g of a 10% dispersion of a cellulosic powder (Solka-Floc from Brown Co.) with 20 drops of concentrated nitric acid and then sensitized with 0.4 cc of silver nitrate solution (1 g/cc). The above was combined with 0.5 g of a 20% gelatin solution. This dispersion was coated (1.4 $g/ft^2$), dried and exposed to air containing

TABLE 10

| | Measured from Exposed Side | | Measured from Film Side | |
|---|---|---|---|---|
| Percent of Exposure | Exposure time (min.) | Reflectance Density | Exposure time (min.) | Reflectance Density |
| 0 | 0 | .03 (0%) | 0 | .15 (0%) |
| 10 | 1.4 | .13 (24%) | 9.2 | .15 (0%) |
| 20 | 2.8 | .21 (43%) | 18.4 | .16 (3%) |
| 30 | 4.2 | .29 (62%) | 27.6 | .17 (5%) |
| 40 | 5.6 | .34 (74%) | 36.8 | .18 (8%) |
| 50 | 7.0 | .38 (83%) | 46.0 | .19 (10%) |
| 60 | 8.2 | .40 (88%) | 55.2 | .20 (13%) |
| 70 | 9.8 | .42 (93%) | 64.4 | .23 (20%) |
| 80 | 11.2 | .43 (95%) | 73.6 | .28 (33%) |
| 90 | 12.6 | .44 (98%) | 82.8 | .37 (55%) |
| 100 | 14.0 | .45 (100%) | 92.0 | .55 (100%) |

35 ppm hydrogen sulfide as previously described. The reflectance density was measured from both sides of the coating. The results are shown in Table 11.

TABLE 11

| | Measured from Exposed Side | | Measured from Film Side | |
|---|---|---|---|---|
| Percent of Exposure | Exposure time (min.) | Reflectance Density | Exposure time (min.) | Reflectance Density |
| 0 | 0 | .30 (0%) | 0 | .47 (0%) |
| 10 | 1.5 | .36 (21%) | .7 | .47 (0%) |
| 20 | 3.0 | .42 (41%) | 1.4 | .48 (9%) |
| 30 | 4.5 | .46 (55%) | 2.1 | .49 (18%) |
| 40 | 6.0 | .49 (66%) | 2.8 | .50 (27%) |
| 50 | 7.5 | .52 (76%) | 3.5 | .51 (36%) |
| 60 | 9.0 | .54 (83%) | 4.2 | .53 (55%) |
| 70 | 10.5 | .56 (90%) | 4.9 | .55 (72%) |
| 80 | 12.0 | .57 (93%) | 5.6 | .57 (91%) |
| 90 | 13.5 | .58 (97%) | 6.3 | .57 (91%) |
| 100 | 15.0 | .59 (100%) | 7.0 | .58 (100%) |

A coating dispersion was prepared by acidifying 25 g of a 40% titanium dioxide dispersion with 5 drops of concentrated nitric acid solution and then sensitized with 0.5 cc of silver nitrate solution (1 g/cc). The above was combined with 1.65 g of 20% gelatin solution and 2 cc of ethanol. This dispersion was coated (3.2 g/ft$^2$), dried and exposed to air containing 35 ppm hydrogen sulfide as previously described. The refelectance density was measured from both sides of the coating. The results are shown in Table 12.

TABLE 12

| | Measured from Exposed Side | | Measured from Film Side | |
|---|---|---|---|---|
| Percent of Exposure | Exposure time (min.) | Reflectance Density | Exposure time (min.) | Reflectance Density |
| 0 | 0 | .01 (0%) | 0 | .13 (0%) |
| 10 | .9 | .08 (24%) | 6.2 | .14 (3%) |
| 20 | 1.8 | .14 (44%) | 12.4 | .15 (6%) |
| 30 | 2.7 | .19 (59%) | 18.6 | .17 (11%) |
| 40 | 3.6 | .23 (76%) | 24.8 | .19 (16%) |
| 50 | 4.5 | .26 (86%) | 31.0 | .22 (24%) |
| 60 | 5.4 | .27 (90%) | 37.2 | .25 (32%) |
| 70 | 6.3 | .28 (93%) | 43.4 | .29 (43%) |
| 80 | 7.2 | .29 (97%) | 49.6 | .35 (59%) |
| 90 | 8.1 | .29 (97%) | 55.8 | .44 (84%) |
| 100 | 9.0 | .31 (100%) | 62.0 | .50 (100%) |

A coating dispersion was prepared by acidifying 20 g of a 50% calcium sulfate dispersion with 5 drops of concentrated nitric acid solution and then sensitized with 0.5 cc of silver nitrate solution (1 g/cc). The above was combined with 1.65 g of 20% gelatin solution and 2 cc of ethanol. This dispersion was coated (6.1 g/ft$^2$), dried and exposed to air containing 35 ppm hydrogen sulfide as previously described. The reflectance density was measured from both sides of the coating. The results are shown on Table 13.

TABLE 13

| | Measured from Exposed Side | | Measured from Film Side | |
|---|---|---|---|---|
| Percent of Exposure | Exposure time (min.) | Reflectance Density | Exposure time (min.) | Reflectance Density |
| 0 | 0 | .10 (0%) | 0 | .21 (0%) |
| 10 | 2 | .18 (20%) | 3.5 | .22 (4%) |
| 20 | 4 | .25 (38%) | 7.0 | .24 (11%) |
| 30 | 6 | .32 (55%) | 10.5 | .26 (18%) |
| 40 | 8 | .37 (68%) | 14.0 | .29 (29%) |
| 50 | 10 | .41 (78%) | 17.5 | .33 (48%) |
| 60 | 12 | .44 (85%) | 21.0 | .38 (61%) |
| 70 | 14 | .47 (93%) | 24.5 | .42 (75%) |
| 80 | 16 | .48 (95%) | 28.0 | .45 (86%) |
| 90 | 18 | .49 (98%) | 31.5 | .47 (93%) |
| 100 | 20 | .50 (100%) | 35.0 | .49 (100%) |

A coating dispersion was prepared by acidifying 20 grams of a 50% barium titanate dispersion with 5 drops of concentrated nitric acid solution and then sensitized with 0.5 cc of silver nitrate solution (1 g/cc). The above was combined with 1.65 g of 20% gelatin solution and 2 cc of ethanol. This dispersion was coated (6.5 g/ft$^2$), dried, and exposed to air containing 35 ppm hydrogen sulfide as previously described. The reflectance density was measured from both sides of the coating. The results are shown in Table 14.

TABLE 14

| | Measured from Exposed Side | | Measured from Film Side | |
|---|---|---|---|---|
| Percent of Exposure | Exposure time (min.) | Reflectance Density | Exposure time (min.) | Reflectance Density |
| 0 | 0 | .09 (0%) | 0 | .22 (0%) |
| 10 | 3 | .26 (43%) | 4.2 | .25 (7%) |
| 20 | 6 | .34 (63%) | 8.4 | .30 (17%) |
| 30 | 9 | .38 (73%) | 12.6 | .35 (28%) |
| 40 | 12 | .40 (78%) | 16.8 | .41 (41%) |
| 50 | 15 | .42 (83%) | 21.0 | .47 (54%) |
| 60 | 18 | .44 (88%) | 25.2 | .54 (70%) |
| 70 | 21 | .46 (93%) | 29.4 | .59 (80%) |
| 80 | 24 | .47 (95%) | 33.6 | .64 (91%) |
| 90 | 27 | .48 (98%) | 37.8 | .67 (98%) |
| 100 | 30 | .49 (100%) | 42.0 | .68 (100%) |

A coating sensitive to sulfur dioxide was prepared by ball milling for eight hours, a dispersion of 75 grams magnesium oxide (Merck Maglite A), 75 grams of alumina, (Reynolds RA-1 (8×16 mesh) ball milled in ethanol and dried), 2 grams of the sodium salt of indophenol as the sensitizer, 10 grams of polyvinyl butyral (Butvar B-76 Monsanto Chemicals) as the binder in a solvent of 300 grams of toluene and 50 grams butanol.

This dispersion was coated on a polyester film and dried. Using a monitoring device as previously described, the coating (2.62 grams/ft$^2$) was exposed to 50 ppm sulfur dioxide. The reflectance color density was measured as a function of exposure time on both sides of the coating. The results are tabulated in Table 15.

TABLE 15

| | Measured from Exposed Side | | Measured from Film Side | |
|---|---|---|---|---|
| Percent of Exposure | Exposure Time (Min.) | Reflectance Density | Exposure Time (Min.) | Reflectance Density |
| 0 | 0 | 1.13 (0%) | 0 | 1.15 (0%) |
| 10 | 4 | .62 (61%) | 6.2 | 1.15 (0%) |
| 20 | 8 | .53 (72%) | 12.4 | 1.14 (1%) |
| 30 | 12 | .47 (80%) | 18.6 | 1.14 (1%) |
| 40 | 16 | .43 (84%) | 24.8 | 1.12 (4%) |
| 50 | 20 | .39 (89%) | 31.0 | 1.06 (12%) |
| 60 | 24 | .36 (93%) | 37.2 | .96 (25%) |
| 70 | 28 | .34 (95%) | 43.4 | .76 (52%) |
| 80 | 32 | .32 (98%) | 49.6 | .56 (79%) |
| 90 | 36 | .31 (99%) | 55.8 | .44 (95%) |
| 100 | 40 | .30 (100%) | 62.0 | .40 (100%) |

A coating sensitive to chlorine was prepared by ball milling for 12 hours a coating dispersion of 8.56 g of a silica pigment (Syloid 244 from W. R. Grace Co., a Division of Davidson Chemicals) with 2.32 g of a polyvinyl butyral binder (Butvar B-76 from Monsanto Chemicals) and 29.1 g of toluene. This coating dispersion was sensitized with 0.5 g of N-benzoyl leuco methylene blue and coated on a polyester film and dried. Using a monitoring device as previously described, the coating (2.65 grams/ft$^2$) was exposed to 10 ppm chlorine. The reflectance color density was measured on the side of the coating exposed to chlorine as well as the film side. The results are tabulated in Table 16.

TABLE 16

| | Measured from Exposed Side | | Measured from Film Side | |
|---|---|---|---|---|
| Percent of Exposure | Exposure Time (Min.) | Reflectance Density | Exposure Time (Min.) | Reflectance Density |
| 0 | 0 | .07 (0%) | 0 | .32 (0%) |
| 10 | 2 | .24 (25%) | 2.9 | .34 (5%) |
| 20 | 4 | .36 (43%) | 5.8 | .37 (13%) |
| 30 | 6 | .47 (59%) | 8.7 | .40 (20%) |
| 40 | 8 | .55 (71%) | 11.6 | .43 (28%) |
| 50 | 10 | .61 (79%) | 14.5 | .48 (40%) |
| 60 | 12 | .65 (85%) | 17.4 | .54 (55%) |
| 70 | 14 | .69 (91%) | 20.3 | .60 (70%) |
| 80 | 16 | .72 (96%) | 23.2 | .67 (88%) |
| 90 | 18 | .74 (99%) | 26.1 | .70 (98%) |
| 100 | 20 | .75 (100%) | 29.0 | .71 (100%) |

A coating sensitive to sulfur dioxide was prepared by ball milling 10 grams of silica (Syloid 244 from W. R. Grace) with 20 grams titanium dioxide in 100 grams of toluene and 50 grams butanol. To this dispersion was added 1 gram of potassium hydroxide, 2 grams of the sensitizer, the sodium salt of indophenol and 6 grams of the binder, polyvinyl butyral (Butvar B-76 from Monsanto). This dispersion was coated (1.8 g/ft$^2$), dried and exposed to air containing 50 ppm sulfur dioxide as previously described. The reflectance density was measured from both sides of the coating. The results are shown in Table 17.

TABLE 17

| | Measured from Exposed Side | | Measured from Film Side | |
|---|---|---|---|---|
| Percent of Exposure | Exposure Time (Min.) | Reflectance Density | Exposure Time (Min.) | Reflectance Density |
| 0 | 0 | .65 (0%) | 0 | .74 (0%) |
| 10 | 1.5 | .44 (53%) | 2.6 | .74 (0%) |
| 20 | 3.0 | .38 (68%) | 5.2 | .74 (0%) |
| 30 | 4.5 | .34 (78%) | 7.8 | .74 (0%) |
| 40 | 6.0 | .31 (85%) | 10.4 | .73 (3%) |
| 50 | 7.5 | .29 (90%) | 13.0 | .72 (8%) |
| 60 | 9.0 | .28 (93%) | 15.6 | .66 (32%) |
| 70 | 10.5 | .27 (95%) | 18.2 | .58 (64%) |
| 80 | 12.0 | .26 (98%) | 20.8 | .54 (80%) |
| 90 | 23.5 | .26 (98%) | 23.4 | .51 (92%) |
| 100 | 15.0 | .25 (100%) | 26.0 | .49 (100%) |

The effect on image development and its endpoint resolution with respect to the selected pigment was investigated by using a combination of pigments. Two pigment dispersions were prepared. One as formulated in Table 4 and another with 16% of the alumina replaced with chromic oxide, a green pigment. Each was combined with binder solution and formulated as coating dispersion E in Table 4. The coatings were prepared and dried as previously described. Coatings were selected and exposed to 35 ppm hydrogen sulfide. The reflectance color density as a function of exposure time is shown in Table 18.

TABLE 18

| | Pigment Alumina/Chromic Oxide | | Pigment Alumina | |
|---|---|---|---|---|
| Percent of Exposure | Exposure Time (Min.) | Reflectance Density | Exposure Time (Min.) | Reflectance Density |
| 0 | 0 | .49 (0%) | 0 | .23 (0%) |
| 10 | 10.5 | .50 (3%) | 7.4 | .24 (2%) |
| 20 | 21.0 | .51 (6%) | 14.8 | .25 (5%) |
| 30 | 31.5 | .52 (9%) | 22.2 | .27 (9%) |
| 40 | 42.0 | .53 (12%) | 29.6 | .30 (16%) |
| 50 | 52.5 | .54 (16%) | 37.0 | .32 (21%) |
| 60 | 63.0 | .55 (19%) | 44.4 | .35 (28%) |
| 70 | 73.5 | .56 (22%) | 51.8 | .38 (35%) |
| 80 | 84.0 | .58 (28%) | 59.2 | .41 (42%) |
| 90 | 94.5 | .66 (53%) | 66.6 | .48 (58%) |
| 100 | 105.0 | .81 (100%) | 74.0 | .66 (100%) |

It will be seen that the initial reflectance color density of the green (alumina/chromic oxide) coating is greater than the alumina coating and the density change to its final value is correspondingly smaller. However, the greater portion of the density change occurs during the final stages of the image development as with the alumina pigment material. The increased hiding power of the green pigment coating thus allows for more vivid visual determination of the exposure endpoint and is particularly useful where the visual acuity of the observer is not well developed.

What is claimed is:

1. Indicator material for the quantitative detection of low concentrations of a selected hazardous material in ambient air comprising a pigment material, a binder and a sensitizer, reactive with said selected hazardous material, coated upon a transparent substrate as porous coating permitting gaseous diffusion of said selected hazardous material thereinto, said pigment material and binder being present in a ratio of about 5:1 to about 40:1, said indicator material upon exposure to said selected hazardous material undergoing an irreversible chemical reaction which progresses, as a function of diffusion, layer-wise through the depth of the coating until it reaches the transparent substrate resulting in a visually resolvable color change viewed through said transparent substrate, said reaction rate being proportional to the sensitizer concentration and the coating weight, said reaction in said coating being initially gradual and becoming more rapid as it approaches its final value thus indicating that exposure to said selected hazardous material has reached a selected time-weighted-average value.

2. Indicator material according to claim 1 wherein the hazardous material is hydrogen sulfide and the sensitizer in AgNO$_3$.

3. Indicator material according to claim 1 wherein the hazardous material is sulfur dioxide and the sensitizer is indophenol.

4. Indicator material according to claim 1 wherein the hazardous material is chlorine and the sensitizer is N-benzoyl leuco methylene blue.

5. Indicator material according to claim 1 wherein the pigment material is activated alumina.

6. Indicator material according to claim 1 wherein the pigment material is silica.

7. Indicator material according to claim 1 wherein the pigment material is a combination of alumina and chromic oxide.

8. Indicator material according to claim 1 wherein the pigment material is lead chromate.

9. Indicator material according to claim 1 wherein the pigment material is cellulosic powder.

10. Indicator material according to claim 1 wherein the pigment material is titanium dioxide.

11. Indicator material according to claim 1 wherein the pigment material is calcium sulfate.

12. Indicator material according to claim 1 wherein the pigment material is barium titanate.

13. Indicator material according to claim 1 wherein the pigment material is a combination of alumina and magnesium oxide.

14. Indicator material according to claim 1 wherein the pigment material is a combination of silica and titanium dioxide.

15. Indicator material according to claim 1 wherein the binder is a gelatin.

16. Indicator material according to claim 1 wherein the binder is polyvinyl butyral.

* * * * *